United States Patent [19]
Rosenthal et al.

[11] Patent Number: 5,897,573
[45] Date of Patent: Apr. 27, 1999

[54] RADIOACTIVE MEDICAL SUTURE AND METHOD OF MAKING THE SAME

[76] Inventors: David Rosenthal, 341 Lands Mill SE., Marietta, Ga. 30067; Stephen A. Sosnowski, 2958 Ora Avo Ter., Vista, Calif. 92084

[21] Appl. No.: 08/837,710

[22] Filed: Apr. 22, 1997

Related U.S. Application Data

[60] Provisional application No. 60/016,360, Apr. 26, 1996.
[51] Int. Cl.[6] ..................................................... A61B 17/04
[52] U.S. Cl. ............................... 606/224; 606/228; 600/3
[58] Field of Search ................... 600/1, 3; 606/222–224, 606/228

[56] References Cited

U.S. PATENT DOCUMENTS 3,943,933  3/1976  Gertzman ................................. 606/224

OTHER PUBLICATIONS

Intracoronary Irradiation Markedly Reduces Restenosis After Balloon Angioplasty in a Porcine Model, Journal of the American College of Cardiology, vol. 23, No. 6, pp. 1491–1498, May 1994; Joseph G. Wiedermann, MD, Charles Marboe, MD, Howard Amols, PhD, Allan Schwartz, MD, FACC, Judah Weinberger, MD, PhD, FACC.

High Dose Rate Brachytherapy For Prevention Of Restenosis After Percutaneous Transluminal Coronary Angioplasty: Preliminary Dosimetric Test Of A New Source Presentation, Int. J. Radiation Biol. Phys., vol. 33, No. 1, pp. 211–215, 1995; Youri Popowski, M.D., Vitali Verin, M.D., Igor Papirov, Philippe Nouet, Michel Rouzand, Eugene Grob, Michael Schwager, Philippe Urban, M.D., Wilhelm Rutishauser, M.D. and John M. Kurtz, M.D.

Endovascular Irradiation—A New Method To Avoid Recurrent Stenosis After Stent Implantation In Peripheral Arteries: Technique And Preliminary Results, Int. J. Radiation Oncology Biol. Phys, vol. 29, No. 1, pp. 183–186, 1994; H.D. Bottcher, M.D., B. Schopohl, M.D., D. Liermann, M.D., J. Kollath, M.D. and I.A. Adamietz, M.D.

Prophylactic Endovascular Radiotherapy to Prevent Intimal Hyperplasia after Stent Implantation in Femoropopliteal Arteries, CardioVascular and Interventional Radiology, vol. 17, pp. 12–16, 1994; Dieter Liermann, Heinz D. Bottcher, Jürgen Kollath, Bernd Schopohl, Gerd Strassman, Ernst P. Strecker, Karl H. Breddin.

*Primary Examiner*—Gary Jackson
*Attorney, Agent, or Firm*—Thomas, Kayden, Horstemeyer & Risley

[57] ABSTRACT

A radioactive suture for inhibiting an intimal hyperplastic response comprises a needle and a suture material having a radioactive beta-emitting element. This radioactive element is preferably chemically bonded to an organic substrate of the suture material. It is preferred that the radioactive suture material generates a beta radiation greater than 0.0002 uCi/cm. A first preferred method for producing the radioactive suture comprises the steps of placing the suture needle and the suture material in a sealed reaction chamber. Once the suture is in the reaction chamber, an ionized beta radiation emitting element, preferably ionized tritium, is introduced into the chamber. While in the chamber, an entropic exchange process begins wherein the beta radiation emitting element is exchanged for hydrogen molecules in the organic suture material. Once the desired level of tritium or other beta radiation emitting element is incorporated in the suture material, the reaction chamber is flushed. The suture is then rinsed, dried, removed from the reaction chamber, and packaged. In another aspect, a radioactive suture may be fabricated from an organic polypropylene material. A beta radiation emitting element, preferably tritium, is incorporated directly into a backbone of the organic polypropylene material. The now radioactive polypropylene material is extruded into a suture thread, which is attached to a suture needle and packaged for shipment and later use. Although not required by the present inventive method, the preferred embodiment of the organic polypropylene material comprises carbon 12.

11 Claims, No Drawings

RADIOACTIVE MEDICAL SUTURE AND METHOD OF MAKING THE SAME

RELATED APPLICATION

This application is based upon, and claims priority to prior-filed provisional application Ser. No. 60/016,360; filed Apr. 26, 1996.

FIELD OF THE INVENTION

The present invention relates generally to medical sutures for bringing together ends of biological tissue and, more particularly, to an apparatus and method for making a radioactive medical suture having beta radiation emitting capabilities for inhibiting an intimal hyperplastic response.

BACKGROUND OF THE INVENTION

Sutures are used to bring together ends of biological tissue and hold them in place until the joining tissues have time to heal. In patients with arterial occlusive disease, vascular surgeons use sutures to anastomose autogenous vein, prostehtic grafts, or arteries to other arteries in order to bypass around or replace diseased arterial segments. At virtually all inastomotic sites between the arteries and autogenous vein, or prosthetic grafts, a condition of rapid cellular growth termed "intimal hyperplasia" may occur.

Intimal hyperplasia (hereinafter "IH") is the usual response to blood vessel injury. This rapid cellular growth, as a response to injury of the blood vessel cellular lining (intima), begins to narrow (stenose) the opening (lumen) between the vessels and/or graft to the point where an occlusion may occur. More specifically, IH forms as a result of smooth muscle cell proliferation, migration, and extracellular matrix deposition. The interaction of platelets, macrophages, growth factors, and cytokines plays an important role in the process. There are systemic regimens to prevent the intimal hyperplatic response in animal models but none has proven beneficial in humans. IH is the primary cause of "restenosis" (narrowing) in the first year after vascular bypass operations and may cause indwelling venous catheters to occlude as well. Usually, the patient must have another operation to revise or replace the occluded graft. If a major vein occludes (i.e. jugular or subclavian) massive edema of the upper extremity, face and neck may occur and if an artery occludes, it could possibly lead to potential limb loss.

The most frequently performed prosthetic graft operation is an arterial to venous conduit for dialysis in chronic renal failure patients. Renal dialysis patients require repetitive angioaccess to this arterial-venous graft for dialysis to rid their system of toxins. The most commonly used graft for dialysis is a synthetic graft made from teflon or ePTFE (expanded polytetrafluroethylene). Unfortunately, these grafts rapidly fail and have a primary occlusion rate of 15% to 50% during the first year, with a mean patency of only 15 months. This failure in most cases is due to the development of intimal hyperplasia at the venous anastomosis.

In recent years studies have been conducted in animal models whose vessels have undergone angioplasty. It was found that the vessels response to injury from balloon angioplasty is similar to that observed at suture anastomotic lesions. Studies conducted at Emory University and Vanderbilt University suggest that "restenosis" (narrowing) results primarily from the migration and rapid proliferation of a smooth muscle type cell after balloon angioplasty. It has been demonstrated by these groups that very low levels of beta-particle irradiation introduced to the site of injury following angioplasty markedly inhibits smooth muscle cell proliferation and or migration. In a series of tissue culture experiments a 0.20 mm diameter titaniumwire was impregnated with low concentrations of 32P and these wires were placed in both rat and human smooth muscle cell cultures. The activity level of the wire ranged from 0.002 to 0.06 uCi/cm wire. In comparison to the control with no radiation it was found that in cultures where the wire activity was >0.0006 uCi/cm there was a distinct zone of complete smooth muscle cell inhibition ranging from 5.5 to 10.6 mm from the radioactive wire. It was hypothesized that if a low level radioactive wire could induce such an effect in tissue culture then a stent placed in-vivo could alter or inhibit the restenotic activity in vessels subjected to angioplasty.

Vanderbilt University in conjunction with the Walter Reed Army Medical Center performed a series of experiments in porcine iliac and coronary models utilizing radioactive Strecker stents. First results in iliac model restenosis resulted in a 37% reduction in neointimal area in 32P 0.14 uCi stents vs controls one month post procedure. Further in-vivo testing performed with radioactive Palmaz-Schatz stents in porcine coronary models demonstrated as much as a 50% reduction in neointimal area and cross sectional area of stenosis one month post stent implantation.

Since these early reports, numerous other studies have been conducted which have demonstrated and substantiated these early findings.

Thus, there exists a need in the art for a suture having low level radioactive particle emissions for the reduction and possible elimination of smooth muscle cell proliferation and hence neointimal hyperplastic response in anastomotic vessel sites, thereby providing longevity to the life of the graft.

SUMMARY OF THE INVENTION

Briefly described, the present invention comprises a radioactive medical suture and method for making a radioactive medical suture. It is now known that smooth muscle cell proliferation may be inhibited by varying degrees and types of radiation, particularly low level beta radiation. This knowledge is exploited by the novel radioactive medical suture and method described herein. Generally, the present invention utilizes a conventional means of fabricating beta radiation sources using, in the preferred embodiments, tritium as the source initiator.

A preferred embodiment of a radioactive medical suture for inhibiting an intimal hyperplastic response comprises a needle made in a standard manner well known by those skilled in the art. The radioactive suture also comprises a suture material having a radioactive beta-emitting element. This radioactive element is preferably chemically bonded to an organic substrate of the suture material. Although any beta-emitting element is usable with the present invention, the element tritium is the preferred embodiment of the present invention. Generally, tritium is substituted for elemental hydrogen within a polypropylene backbone of a medical suture thereby providing a constant low level source of implantable radiation which will inhibit a neointimal hyperplastic response. It is preferred that the radioactive suture material generates a beta radiation greater than 0.0002 uCi/cm.

A first preferred method for producing the radioactive suture comprises the steps of placing a suture needle and a suture material in a sealed reaction chamber. Once the suture is in the reaction chamber, an ionized beta radiation emitting element is introduced into the chamber. Again, this beta radiation emitting element is preferably tritium. The suture is preferably left in the reaction chamber for one to several weeks. While in the chamber, an entropic exchange process begins wherein the tritium or other beta radiation emitting element is exchanged for hydrogen molecules in the organic suture material.

Once the desired level of tritium or other beta radiation emitting element is incorporated in the suture material, the reaction chamber is flushed by a normal means understood in the art. Then, the suture is rinsed and dried while preferably still in the reaction chamber. The suture is removed from the reaction chamber and packaged as a suture is normally packaged in the art. Such normal packaging usually comprises placing the suture in an aluminum foil, sealed pouch.

Another preferred embodiment of a method for fabricating a radioactive suture initially comprises an organic polypropylene material. A beta radiation emitting element, preferably C12 (carbon 12), is incorporated directly into the backbone of the organic material. As such, a radioactive polypropylene material is created. The polypropylene material is then extruded into a suture thread. This suture thread is then preferably attached to a suture needle and packaged for shipment and later use. Although not required by the present inventive method, in this second preferred embodiment, the organic polypropylene material comprises carbon 12.

Since the source is low level radiation the safety measures required for its handling are minimuim as compared to other radioactive elements, and as the vehicle is a suture, there is no need for injecting or implanting other radioactive substances into a site. Despite the suture's beta radiation emitting characteristics, it does not lose its tensile strength characteristics or other physical properties. The benefits of the beta emitting radiation polymer should not effect normal endothelial cell function, but will inhibit the IH response and therefore, improve graft patency and prevent early graft failure.

Other objects, features and advantages of the present invention will be apparent to those skilled in the art. A more thorough understanding of the invention will be gained through a review of the detailed description set forth below.

DETAILED DESCRIPTION OF THE INVENTION

The present invention relates to a conventional vascular medical suture made from basic monofilament or braided hydrocarbon elements. A typical suture could be made from polypropylene or any other hydrocarbon based suture as is the case in the family Tradename of Prolene surgical sutures made by Johnson and Johnson. Other sutures made by different manufacturers such as Davis and Geck, U.S. Surgical, and other manufacturers could also be used as the backbone carrier for radioactive tritium.

In the first preferred embodiment of the invention, a non-radioactive suture material along with a needle is encapsulated within a sealed reaction chamber. The suture then undergoes incorporation of tritium via the method of Wilzbach. This is a simple process for random labeling of organic molecules with tritium. In this process, ionizing tritium is introduced to the sealed reaction chamber to a level of approximately 15 Ci. Via the entropic exchange process of tritium for hydrogen, the tritium is substituted into the organic matrix of the suture.

The suture in the sealed reaction chamber is kept in the tritium ionizing field for a period of a day to several weeks depending on the amount of tritium desired to be incorporated and the activity level of the suture required. Upon completion of the reaction, the reaction chamber is flushed in a usual fashion understood by those skilled in the art and the suture rinsed, dried and removed. Because of the low amount of beta radiation, handling of the suture requires only the use of latex gloves. Packaging the suture in a common aluminum foil suture pouch is sufficient to contain the radioactivity of the incorporated tritium.

A second preferred embodiment to the invention comprises fabricating a suture from a radioactive polypropylene material. In this embodiment, radioactive polypropylene is synthesized from its elemental components. In this method, tritium or other beta radiating emitting element is incorporated directly within the backbone of the organic compound. The element of choice in this configuration would be C12 (carbon 12). Once the radioactive compound has been formulated, it is then extruded to the desired thread thickness and attached to a needle in a conventional fashion and packaged. The drawback with this process is that it creates a lot of radioactive exposed equipment that must be cleaned and properly handled.

It would be apparent to one skilled in the art that many variations and modifications may be made to the preferred embodiment as described above without substantially departing from the principles of the present invention. Such variations and modifications are intended to be included herein and are within the scope of the present invention, as set forth in the following claims.

What is claimed is:

1. A radioactive suture apparatus for inhibiting an intimal hyperplastic response, said suture apparatus comprising:
   (a) a needle; and
   (b) a suture material affixed to said needle, said suture material having a radioactive beta-emitting element chemically bonded to an organic substrate of said suture material, wherein said suture material generates a beta radiation greater than 0.0002 uCi/cm.

2. The radioactive suture of claim 1, wherein said needle is affixed to said suture material prior to incorporation of a beta radiation emitting means.

3. The radioactive suture of claim 1, wherein said needle is affixed to said suture material after incorporation of a beta-radiation emitting means.

4. The radioactive suture of claim 1, wherein said suture material comprises an extruded radioactive polypropylene material.

5. The radioactive suture of claim 1, wherein said radioactive beta-emitting element comprises tritium.

6. A method for producing a radioactive suture for inhibiting an intimal hyperplastic response, said method comprising the steps of:
   (a) providing a sealed reaction chamber;
   (b) placing a needle and a suture material in said chamber; and
   (c) introducing an ionized beta radiation emitting element into said chamber for causing an entropic exchange process of said beta radiation emitting element for hydrogen in said suture material.

7. The method of claim 6, further comprising the steps of:
   (d) flushing said reaction chambers;
   (e) rinsing said suture while said suture is in said reaction chamber;
   (f) drying said suture;
   (g) removing said suture from said reaction chamber; and (h) packaging said suture in a package.

8. The method of claim 7, wherein said beta radiation emitting element comprises ionized tritium.

9. A method for fabricating a radioactive suture having beta emitting tritium, said method comprising a conventional Wilzbach process.

10. A method for fabricating a radioactive suture, said method comprising the steps of:

(a) providing an organic polypropylene material;

(b) incorporating a beta radiation emitting element directly into a backbone of said organic material, whereby a radioactive polypropylene material is created;

(c) extruding said radioactive polypropylene material into a suture thread; and (d) attaching said suture thread to a suture needle.

11. The method of claim 10, wherein said beta radiation emitting element comprises tritium.

* * * * *